United States Patent
Campbell et al.

(12)

(10) Patent No.: US 6,262,035 B1
(45) Date of Patent: Jul. 17, 2001

(54) GENE REPLACEMENT THERAPY FOR MUSCULAR DYSTROPHY

(75) Inventors: Kevin P. Campbell, Iowa City; Kathleen H. Holt, Corlville; Franck Duclos; Leland E. Lim, both of Iowa City; Volker Straub, Essen; Beverly Davidson; Roger Williamson, both of Iowa City, all of IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/164,664

(22) Filed: Oct. 1, 1998

(51) Int. Cl.$^7$ .............................. A01N 43/04; C12N 15/00; C12N 15/63
(52) U.S. Cl. ..................... 514/44; 435/320.1; 435/455
(58) Field of Search ........................... 514/44; 435/320.1, 435/325

(56) References Cited

FOREIGN PATENT DOCUMENTS

| 95 05738 | 3/1995 | (WO) . |
| 99 43360 | 9/1999 | (WO) . |

OTHER PUBLICATIONS

Eck et al., Goodman & Gilman's The Pharmacological Basis of Therapeutics, Ninth Edition, McGraw–Hill, New York, p. 77–101, 1996.*
Bartlett et al., Gene Therapy, edited by Lemoine et al., Bios Scientific Publishers Ltd, Oxford, p. 77–92, 1996.*
Holt et al., *Mol. Biol. 1*: 841–848 (1998).
Duclos et al., *J. of Cell Biol. 142*: 1461–1471 (1998).
Nigro et al., *Nature Gen. 4*: 195–198 (1996).
Coral–Vazquez et al., *Cell 98*: 465–474 (1999).
Crosbie et al., *J. Biol. Chem. 272*: 31221–31224 (1997).
Roberds et al., *Cell 78*: 625–633 (1994).
Piccolo et al., *Nature Genet. 10*: 243–245 (1995).
Lim et al., *Nature Genet. 11*: 257–265 (1995).
Bonneman et al., *Nature Genet. 11*: 266–273 (1995).
Noguchi et al., *Science 270*: 819–822 (1995).
Passo–Bueno et al., *Hum. Mol. Genet. 5*: 815–820 (1996).
Nigro et al., *Hum. Mol. Genet. 5*: 1179–1186 (1996).
Nigro et al., *Nature Genet. 14*: 195–198 (1996).
Okazaki et al., *Nature Genet. 13*: 87–90 (1996).
Nigro et al., *Hum. Mol. Genet. 6*: 601–607 (1997).
Sakamoto et al., *Proc. Natl. Acad. Sci. 94*: 13873–13878 (1997).
Piccolo et al., *J. Med. Genet. 34*: 470–475 (1997).
Duggan et al., *N. England J. Med. 336*: 618–624 (1997).
Carrié et al., *J. Med. Genet. 34*: 470–475 (1997).
Ervasti et al., *Cell 66*: 1121–1131 (1991).
Yoshida et al., *Eur. J. Biochem. 222*: 1055–1061 (1994).
Jung et al., *FEBS 381*: 15–20 (1996).
Holt et al., Molecular Cell, vol. 1, p. 841–848, May 1998.*
Mastrangelo et al., Seminars in Oncology, vol. 23(1), p. 4–21, Feb. 1996.*
Orkin et al., Report and Recommendation of the Panel to Assess the NIH investment in Research on Gene Therapy, Dec. 1995.*
Duclos et al., The Journal of Cell Biology, vol. 142(6), p. 1461–1471, Sep. 1998.*
pg,8*
Van Der Kooi et al., Muscle and Nerve, vol. 21(5), p. 584–590, May 1998.*
Karpati et al., Clinical Genetics, vol. 55, p. 1–8, 1999.*

* cited by examiner

*Primary Examiner*—Deborah J. R. Clark
*Assistant Examiner*—Shin-Lin Chen
(74) *Attorney, Agent, or Firm*—Farrell & Associates, P.C.; Kevin M. Farrell; Shayne Y. Huff (57) ABSTRACT

Disclosed is a method for treating a patient suffering from the disease sarcoglycan-deficient limb-girdle muscular dystrophy by gene replacement therapy. Sarcoglycan gene replacement therapy produces extensive long-term expression of the sarcoglycan species which restores the entire sarcoglycan complex, results in the stable association of alpha-dystroglycan with the sarcolemma, and eliminates the morphological markers of limb-girdle muscular dystrophy. In another aspect, the invention relates to a method for determining a specific defective sarcoglycan species in the tissue of a patient. The method involves culture of muscle cells obtained from the patient, and the independent introduction of expression vectors encoding each of the sarcoglycan species, α, β, γ, and δ, into the cultured cells with subsequent assaying for restoration of the dystrophin-glycoprotein complex. In another aspect, the invention relates to a mouse, and cells derived therefrom, homozygous for a disrupted α-sarcoglycan gene. The disruption prevents the synthesis of functional α-sarcoglycan in cells of the mouse and results in the mutant mouse having no detectable sarcospan, β-, γ-, δ-sarcoglycan, and reduced α-dystroglycan in the sarcolemma of skeletal and cardiac muscles, and a reduction of dystrophin in skeletal muscle, when compared to tissue of a mouse lacking a disrupted α-sarcoglycan gene. In another aspect, the invention relates to methods for screening for therapeutic agents useful in the treatment of sarcoglycan-deficient limb-girdle muscular dystrophy. The methods involve administering a candidate therapeutic agent to a mouse, or cells derived therefrom, and assaying for therapeutic effects on the mouse or cells, with the determination of therapeutic effects being a reduction or reversal in disease progression, or a restoration of the dystroglycan complex.

6 Claims, 5 Drawing Sheets

SEQUENCE LISTING

<160> NUMBER OF SEQ ID NOS: 8

<210> SEQ ID NO 1
<211> LENGTH: 18
<212> TYPE: PRT
<213> ORGANISM: Homo sapiens

<400> SEQUENCE: 1

Met Met Pro Gln Glu Gln Tyr Thr His His Arg Ser Thr Met Pro Gly
 1               5                   10                  15

Ala Ala

<210> SEQ ID NO 2
<211> LENGTH: 31
<212> TYPE: DNA
<213> ORGANISM: Artificial Sequence

```
<220> FEATURE:
<223> OTHER INFORMATION: Description of Artificial Sequence:PCR primer
      for analysis

<400> SEQUENCE: 2
cccctcgagc cgttcctcag actttttatt c                              31

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:PCR primer
      for analysis

<400> SEQUENCE: 3
aatgcggccg ctctcctgta cgaacat                                   27

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:PCR primer
      for analysis

<400> SEQUENCE: 4
cagggctggg agctgggttc tg                                        22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:PCR primer
      for analysis

<400> SEQUENCE: 5
cccagggcct tgatgcct                                             18

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:PCR primer
      for analysis

<400> SEQUENCE: 6
gctatcagga catagcgttg gcta                                      24

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: polypeptide
      fragment for use as antigen

<400> SEQUENCE: 7

Cys Phe Val Met Trp Lys His Arg Tyr Gln Val Phe Tyr Val Gly Val
  1               5                  10                  15

Gly Leu Arg Ser Leu Met Ala Ser Asp Gly Gln Leu Pro Lys Ala
             20                  25                  30

<210> SEQ ID NO 8
```

```
-continued

<211> LENGTH: 17
<212> TYPE: PRT
<213> ORGANISM: Artificial Sequence
<220> FEATURE:
<223> OTHER INFORMATION: Description of Artificial Sequence:polypeptide
      fragment for use as antigen

<400> SEQUENCE: 8

Pro His Gln Thr Gln Ile Pro Gln Gln Gln Thr Thr Gly Lys Trp Tyr
 1               5                  10                  15

Pro
```

GENE REPLACEMENT THERAPY FOR MUSCULAR DYSTROPHY

BACKGROUND OF THE INVENTION

The term muscular dystrophy describes a group of diseases characterized by hereditary progressive muscle weakness and degeneration. Several muscular dystrophies are caused by mutations in genes that encode sarcolemmal proteins, including certain types of limb-girdle muscular dystrophy (LGMD). LGMD is genetically and clinically heterogeneous; it may be inherited in an autosomal dominant or recessive manner, and may have different rates of progression and severity. A unifying theme among the LGMDs is the initial involvement of the shoulder and pelvic girdle muscles, with relative sparing of most other muscle groups (Jackson et al., *Pediatrics* 41, 495–501 (1968); Bushby, K. M., *Neuromusc Disord* 5, 71–74 (1995)).

The pace of discovery in the field of muscular dystrophy research has been rapid since the discovery of the Duchenne and Becker muscular dystrophy (DMD) gene in 1986 (Monaco et al., *Nature* 323, 646–650 (1986)). The DMD gene encodes dystrophin, a large cytoskeletal protein that together with other molecular components makes up the dystrophin-glycoprotein complex (DGC). The dystrophin-glycoprotein complex (DGC) is a large oligomeric complex of sarcolemmal proteins and glycoproteins in skeletal and cardiac muscle (Campbell, K. P. *Cell* 80, 675–679 (1995); Ozawa et al., *Hum. Mol. Genet.* 4, 1711–1716 (1995)). This complex consists of dystrophin, a large cytoskeletal protein which binds F-actin; α- and β-dystroglycan, which bind laminin and the cysteine-rich region of dystrophin, respectively; α-, β-, γ-, and δ-sarcoglycan (δ-SG), which form a distinct subcomplex; and sarcospan, a 25 kDa protein predicted to span the membrane four times (Crosbie et al., *J. Biol. Chem.* 272, 31221–31224 (1997). The DGC spans the sarcolemma and is believed to play an essential role in maintaining the normal architecture of the muscle sarcolemma by constituting a link between the subsarcolemmal cytoskeleton and the extracellular matrix. This structural linkage is thought to protect muscle fibers from the mechanical stress of contraction.

Mutations in different components of the DGC lead to similar dystrophic features, suggesting that the function of the DGC as a whole is dependent on intact molecular interactions between its individual subunits. The loss of one component destroys the link, and leads to muscle fiber degeneration. Several components of the DGC have been implicated in several human muscular dystrophies (Straub et al., *Curr. Opin. Neurol.* 10, 168–175 (1997)). Mutations in dystrophin cause Duchenne and Becker muscular dystrophy (DMD) (Hoffman et al., *Cell* 51, 919–928 (1987)). Two forms of congenital muscular dystrophy are caused by mutations in the extracellular matrix protein laminin 2 (Helbling-Leclerc et al., *Nature Genet.* 11, 216–218 (1995); Allamand et al., *Hum. Mol. Genet.* 6, 747–752 (1997)). Mutations in each of α-, β-, γ-, and δ-SG cause autosomal recessive LGMD types 2D, 2E, 2C, and 2F, respectively (Roberds et al., *Cell* 78, 625–633 (1994); Piccolo et al., *Nature Genet.* 10, 243–245 (1995); Lim et al., *Nature Genet.* 11, 257–265 (1995); Bonneman et al., *Nature Genet.* 11, 266–273 (1995); Noguchi et al., *Science* 270, 819–822 (1995); Passos-Bueno et al., *Hum. Mol. Genet.* 5, 815–820 (1996); Nigro et al., *Hum. Mol. Genet.* 5, 1179–1186 (1996); Nigro et al., *Nature Genet.* 14, 195–198 (1996)).

In the sarcoglycan-deficient LGMDs, a mutation effecting the function of a particular sarcoglycan species leads to the loss or dramatic reduction of all four sarcoglycan proteins from the sarcolemma. Four types of LGMD, LGMD2D, LGMD2E, LGMD2C and LGMD2F, are known to be caused by mutations in distinct sarcoglycan genes, α-, β-, γ- and δ-SG respectively (Roberds et al., *Cell* 78, 625–633 (1994); Piccolo et al., *Nature Genet.* 10, 243–245 (1995); Lim et al., *Nature Genet.* 11, 257–265 (1995); Bonneman et al., *Nature Genet.* 11, 266–273 (1995); Noguchi et al., *Science* 270, 819–822 (1995); Passos-Bueno et al., *Hum. Mol. Genet.* 5, 815–820 (1996); Nigro et al., *Hum. Mol. Genet.* 5, 1179–1186 (1996); Nigro et al., *Nature Genet.* 14, 195–198 (1996)). Unfortunately, functional characterization of the sarcoglycan complex has proven elusive.

The BIO 14.6 hamster is a widely studied animal model of muscular dystrophy and cardiomyopathy (Homburger et al., 1962). In this animal, the sarcoglycan complex is missing and dystrophic features, including central nucleation and necrosis of muscle fibers, are evident. Previous studies have documented a disruption in the integrity of the DGC in skeletal and cardiac muscle of this animal, with a dramatic decrease in the amount of α-dystroglycan (Roberds et al., *J Biol Chem.* 268, 11496–11499 (1993), Iwata et al., *FEBS* 329, 227–231 (1993)). Recently, it was shown that a mutation in the δ-SG gene of BIO 14.6 hamsters leads to sarcoglycan complex disruption and dystrophic changes (Okazaki et al., *Nature Genet.* 13, 87–90 (1996); Nigro et al., *Hum. Mol. Genet.* 6, 601–607 (1997); Sakamoto et al., *Proc. Natl. Acad. Sci.* 94, 13873–13878 (1997)). These findings make the animal a useful model for the study of human sarcoglycan-deficient LGMD.

While the BIO 14.6 hamster model is useful for certain studies, the generation of additional models of sarcoglycan-deficient LGMD would greatly facilitate progress towards understanding of the disease. The use of animal models deficient in the various sarcoglycan species to study the effects of these specific deficiencies, would help identify the exact role of each species in the DGC. Additionally, since there are no known cases of a LGMD from a primary sarcoglycan defect, with concomitant muscular dystrophy and cardiomyopathy, the generation of a phenotypically more accurate model of AR-LGMD would be beneficial to the research effort.

SUMMARY OF THE INVENTION

In one aspect the present invention relates to a method for treating a patient with the disease sarcoglycan-deficient limb-girdle muscular dystrophy by gene replacement therapy. Sarcoglycan gene replacement therapy produces extensive long-term expression of the deficient sarcoglycan species which restores the entire sarcoglycan complex, results in the stable association of alpha-dystroglycan with the sarcolemma, and eliminates the morphological markers of limb-girdle muscular dystrophy.

In another embodiment, the invention relates to a method for determining a specific defective sarcoglycan species in the tissue of a patient. The method involves culture of muscle cells obtained from the patient, and the independent introduction of expression vectors encoding each of the sarcoglycan species, α, β, γ, and δ, into the cultured cells, with subsequent assaying for restoration of the dystrophin-glycoprotein complex.

In another embodiment, the invention relates to a mouse, and cells derived therefrom, that is homozygous for a disrupted α-sarcoglycan gene. The disruption prevents the synthesis of functional α-sarcoglycan in cells of the mouse and results in the mutant mouse having no detectable sarcospan, β-, γ-, δ-sarcoglycan, and having reduced α-dystroglycan in the sarcolemma of skeletal and cardiac muscles, as well as a reduction of dystrophin in skeletal muscle, when compared to tissue of a mouse lacking a disrupted α-sarcoglycan gene.

In another embodiment, the invention relates to methods for screening for therapeutic agents useful in the treatment of sarcoglycan-deficient limb-girdle muscular dystrophy. The methods involve administering a candidate therapeutic agent to a mouse, or cells derived therefrom, and assaying for therapeutic effects on the mouse or cells, with therapeutic effects being a reduction or reversal in disease progression, or a restoration of the dystroglycan complex.

DETAILED DESCRIPTION OF THE INVENTION

The present invention is based on the discovery that sarcoglycan gene replacement can correct primary mutations in individual sarcoglycan components in vivo and lead to the restoration of the DGC. More specifically, experiments in the Exemplification section which follows demonstrate therapeutic delivery of a deficient sarcoglycan gene to produce extensive long-term expression of the sarcoglycan species in animal models. The restored expression of the deficient species rescues the entire sacoglycan complex. This restoration of the sarcoglycan complex results in stable association of alpha-dystroglycan with the sarcolemma and eliminates the morphological markers of limb girdle muscular dystrophy.

One embodiment of the present invention is a method for the treatment of a patient with sarcoglycan-deficient LGMD, caused by a mutation in one of the sarcoglycan species, α, β, γ, or δ, through the expression of the deficient species in the affected tissue from an exogenous source of genetic material encoding the sarcoglycan protein. The deficient sarcoglycan species is determined, and then corrected by introduction of a therapeutic amount of genetic material encoding a functional version of the deficient species, to the affected tissue, under conditions appropriate for expression. The specific sarcoglycan deficiency can be diagnosed by several methods and can be performed to further diagnose a symptomatic individual, or to screen presymptomatic individuals. Such screening includes prenatal screening.

Several mutations in the various sarcoglycan genes have been identified as contributing to LGMD, and others are likely to be identified in the future (Piccolo et al., *Nat. Genet.* 10, 243–245 (1995); Piccolo et al., *J Med Genet.* 34, 470–475 (1997); Duggan, et al., *Neurogenetics* 1, 827–834 (1997); Duggan et al., *N Engl J Med.* 336, 618–624 (1997); Carrier et al., *J Med Genet.* 34, 470–475 (1997)). Mutations that cause a change in expression levels or a change in protein size, such as mutations in transcription or translation regulatory elements, destabilizing point mutations, frame shift, or missense mutations, can be detected by examination of the sarcoglycan proteins themselves via immunodiagnostics of a muscle tissue sample using α, β, γ, or δ-SG specific antibodies (Campbell et al., (1995) U.S. Patent 5,418,139; Campbell et al., (1994) U.S. Pat. No. 5,308,752; Campbell et al., (1997) U.S. Pat. No. 5,672,694), and comparison to wild-type. Alternatively, the genetic material encoding the individual SG genes of a patient can be examined for significant mutations by several different techniques. cDNA or MRNA specific for the individual SG genes can be examined quantitatively for reduction in transcript levels, and also for detectable size differences indicative of frame shift or missense mutations by the techniques of DNA or RNA hybridization analysis, or by amplification using the polymerase chain reaction (PCR).

Mutations can also be identified through sequence analysis of genetic material, by either direct sequencing or probing for specific mutations. Hybridization analysis using nucleic acid probes can identify specific point mutations in a given sarcoglycan gene. Such diagnostic methods are performed by isolating nucleic acids, either genomic DNA, cDNA or mRNA, from an individual and testing the diagnostic probes for the ability to hybridize to the isolated nucleic acid. When necessary, the nucleic acid sequence can be amplified by the PCR prior to hybridization analysis. A working example of this technique uses specific oligonucleotides designed to hybridize to specific mutations in the β-SG gene (Campbell et al., (1997) U.S. Pat. No. 5,672,694). As more mutations in the SG genes are identified as contributing to LGMD, similar oligo probes can be designed and used for rapid diagnostic analysis. In lieu of the development of specific oligo probes, mutations can be identified by sequence analysis of individual SG genes. The genetic material of the individual SG genes can be sequenced, and mutations that would adversely effect expression or protein structure can be identified by comparison to wild type sequences (Campbell et al., (1997) U.S. Pat. No. 5,672,694).

Alternatively, the functional absence of a particular sarcoglycan species can be diagnosed through functional analysis of the cellular complement of sarcoglycan proteins. One example of such an assay is described in detail below.

Once a specific sarcoglycan deficiency is established, a functional replacement gene can be introduced to the effected tissue of the patient, under conditions appropriate for expression. This can be accomplished through the use of an expression vector to deliver sequences that encode a functional SG protein. An appropriate expression vector can safely and efficiently deliver exogenous nucleic acid to a recipient cell in the patient. In order to achieve effective gene therapy, the expression vector used must be designed for efficient cell uptake and gene product expression, e.g. an adenovirus based or adeno-associated virus (AAV) based gene delivery vector (Berkner, K. L., *Current Topics in Microbiol. and Imunol.* 158, 39–66 (1992); Stratford-Perricaudet et al., *Hum. Gene Ther.* 1, 241–256 (1990); Rosenfeld et al. Cell 8, 143–144 (1992); Stratford-Perricaudet et al. *J. Clin. Invest.* 90, 626–630 (1992)). Specific methods of application of the present invention depend largely upon the expression system employed, however, most involve insertion of sarcoglycan coding sequence at an appropriate position within the expression vector, and subsequent delivery of the expression vector to the target tissue for expression.

In the preferred embodiment, a nucleotide sequence encoding the deficient sarcoglycan gene is inserted into an adenovirus based expression vector. Several genes have been successfully expressed using adenovirus based vectors including p53 (Wills et al., *Human Gene Therapy* 5, 1079–188 (1994), dystrophin (Vincent et al., *Nature Genetics* 5, 130–134 (1993), erythropoietin (Descamps et al., *Human Gene Therapy* 5, 979–985 (1994), ornithine transcarbamylase (Stratford-Perricaudet et al., *Hum. Gene Ther.* 1, 241–256 (1990), adenosine deaminase (Mitani et al., *Human Gene Therapy* 5, 941–948 (1994), interleukin-2 (Haddada et al., *Human Gene Therapy* 4, 703–711 (1993), and α-1-antitrypsin (Jaffe et al., *Nature Genetics* 1, 372–378 (1992). The use of adenovirus based vectors in gene therapy is considered promising for a number of reasons, including the wide range of host cells, and the mechanism of expression from the adenoviral vector which occurs without chromosomal integration, eliminating the risk of insertional mutagenesis. Gregory et al., (1997) U.S. Pat. No. 5,670,488; McClelland et al., (1998) U.S. Pat. No. 5,756,086; Armentano et al., (1998) U.S. Pat. No. 5,707,618; Saito et al., (1998) U.S. Pat. No. 5,731,172, herein incorporated by reference, describe several recently developed adenovirus based expression vectors, and their use in gene therapy. Alternatively, a gutted adenovirus delivery system can be used (Clemens et al., *Gene Therapy* 3, 965–972 (1996)).

An adeno-associated virus (AAV) based vector can also be used as a delivery system. Some examples are described by Carter et al., (1989) U.S. Pat. No. 4,797,368; Lebkowski et al., (1992) U.S. Pat. No. 5,153,414; Srivastava et al., (1993) U.S. Pat. No. 5,252,479; Lebkowski et al., (1994) U.S. Pat. No. 5,354,678; Wilson et al., (1998) U.S. Pat. No. 5,756,283, herein incorporated by reference. AAV is an integrating DNA parvovirus, a naturally occurring defective virus that requires other viruses, such as adenovirus or herpes viruses as helper viruses ("Handbook of Parvoviruses", ed., P. Tijsser, CRC Press, (1990)). AAV vectors have been demonstrated functional in a wide variety of cell types, including differentiated and non-dividing cells, suggesting a potential for this vector system for successful in vivo gene delivery to muscle tissue.

Other possible gene expression systems for sarcoglycan gene therapy include retroviral based vectors and delivery systems (Miller et al., *Blood* 76, 271 (1990), and also plasmid based nucleic acid delivery systems (Eastman et al., (1998) U.S. Pat. No. 5,763,270).

In the preferred embodiment, a cytomegalovirus promoter element is used to drive gene expression from the expression vector. However, the expression vector can utilize a variety of regulatory sequences to achieve a therapeutic level of expression. Tissue specific regulatory sequences can also be used to restrict gene expression to a specific target tissue (Kuang et al., *J. Clin. Invest.* 102, 844–852 (1998)).

The method of delivery of the gene expression system to the target tissue varies with the expression system used. In preferred embodiments, upon diagnosis of the deficient sarcoglycan species, an appropriately packaged adenovirus based expression vector construct is delivered via intramuscular injection of the sarcoglycan-deficient muscle tissue. Recipient tissue comprises muscle in the patient that is, or is predicted to be, affected by the sarcoglycan gene deficiency. Administration of the gene to all deficient muscle tissues represents one therapeutic option. However, significant therapeutic benefits can also be achieved by selective administration to specific target muscles, to restore or prevent the loss of specific motor functions. For example, specific treatment of a small number of muscle groups can restore or prevent further deterioration of function, thereby enabling the patient to continue to eat without assistance.

Administration of the deficient sarcoglycan gene should optimally occur at as early a stage in disease progression as diagnosis permits, preferably, prior to the onset of severe muscle damage. Genetic diagnosis of the disease prior to the onset of the pathology allows gene therapy intervention at an extremely early stage in life. Evidence presented in the Exemplification indicates that significant therapeutic benefits may be obtained from such early intervention.

The present invention also provides methods for diagnosing a specific sarcoglycan deficiency of a patient suspected of suffering from sarcoglycan-deficient LGMD. The method is based on the observation that restoration of a single deficient sarcoglycan species can restore the entire sarcoglycan complex and lead to the complete restoration of the DGC. In the preferred embodiment, cells from a biopsy of muscle tissue are propagated in culture under conditions appropriate for the formation of myotubes. An expression vector that encodes one of the sarcoglycan species is introduced to the muscle cells, and the recipient cells are then examined, through either morphological or biochemical assays, for restoration of their dystrophin-glycoprotein complex. Delivery of the deficient sarcoglycan species should produce a functional DGC.

As detailed in the Exemplification section, delivery of a recombinant adenovirus vector expressing δ-SG restores the entire sarcoglycan complex to the naturally δ-SG deficient sarcolemma in BIO 14.6 skeletal muscle, restoring the integrity of the sarcolemma. This restoration produces a coincident stabilization of α-dystroglycan, the extracellular laminin-binding component of the DGC and eliminates characteristic features of disease progression in recipient myofibers. Additionally, injection of a recombinant adenovirus expressing α-sarcoglycan into muscle of a mouse with a homozygous α-SG gene deficiency restores functional sarcoglycan complex to the sarcolemma, further demonstrating the feasibility of gene transfer for the different species of sarcoglycan-deficient-LGMD. These experiments confirm the feasibility of gene delivery therapy to treat sarcoglycan-deficient LGMD. This disclosure constitutes the first example of sarcoglycan gene replacement and demonstrates that primary mutations in individual sarcoglycan components can be corrected in vivo.

Another aspect of the current invention relates to the development of mice with homozygous null mutations in specific sarcoglycan genes that develop a LGMD phenotype. Evidence indicates that a defect in one of either, α-, β-, γ-, or δ-sarcoglycan genes causes sarcoglycan-deficient LGMD (Roberds et al., *Cell* 78, 625–633 (1994); Piccolo et al., *Nature Genet.* 10, 243–245 (1995); Lim et al., *Nature Genet.* 11, 257–265 (1995); Bonneman et al., *Nature Genet.* 11, 266–273 (1995); Noguchi et al., *Science* 270, 819–822 (1995); Passos-Bueno et al., *Hum. Mol. Genet.* 5, 815–820 (1996); Nigro et al., *Hum. Mol. Genet.* 5, 1179–1186 (1996); Nigro et al., *Nature Genet.* 14, 195–198 (1996); Carrie et al., *J Med Genetics* 34, 470–475 (1997)).

One embodiment of the present invention is a mouse, or cell derived therefrom, that is homozygous for a disrupted α-SG gene. The Exemplification outlines the production of a mouse line homozygous for a disrupted α-SG gene, by targeted inactivation of an α-SG allele of an embryonic stem cell, with subsequent implantation into pseudopregnant females to generate heterozygous null progeny. The resulting heterozygous progeny are then subsequently bred to produce homozygous null mutants. This disclosure presents the first engineered animal models for autosomal recessive muscular dystrophy with a primary sarcoglycan deficiency.

Characterization of the resulting α-SG deficient mice (α-SG-/-) indicates that they develop typical histological features of muscular dystrophy including central nucleation, myofibrosis, and necrosis of muscle fibers, and also loss of the entire sarcoglycan complex along with the reduction of α-dystroglycan, sarcospan, and dystrophin from the sarcolemma. Biochemical evidence of the tight association of the sarcoglycan proteins with each other has been previously reported (Ervasti et al., *Cell* 66, 1121–1131 (1991); Yoshida et al., *Eur J Biochem* 222, 1055–1061 (1994); Jung et al., *FEBS* 381, 15–20 (1996)). When taken together, these results indicate that defects in any individual sarcoglycan species which alter primary structure or spatio-temporal synthesis will manifest as defects of the entire sarcoglycan complex, producing a similar phenotype.

α-SG-/- mice have a variety of uses as a murine model system. One such use lies in the identification of therapeutic agents for the treatment of LGMD. To identify therapeutic genes or compounds, candidate agents are delivered to the diseased tissue of the mouse, which is then assayed for reversal of disease pathology, e.g. the elimination of morphological markers for LGMD, restoration of the DGC, restoration of the sarcoglycan complex. Cells isolated from a α-SG-/- mouse can be propagated in culture and used in a similar assay to identify therapeutic agents. SG null mice, or cells derived therefrom, can also be used experimentally to identify functionally significant regions of the deficient sarcoglycan molecules. Such assays involve the re-introduction of the deficient sarcoglycan species, or a portion thereof, with subsequent diagnosis of the treated tissue or cells for restoration of wild type function.

Exemplification
Injection of δ-SG Plasmid DNA Rescues the Sarcoglycan Complex.

To test the hypothesis that δ-SG gene transfer could restore the sarcoglycan complex in the BIO 14.6 hamster, direct plasmid DNA injections into BIO 14.6 skeletal muscle were performed. Previous studies have shown that de novo expression of dystrophin in a small percentage of fibers can be achieved by direct injection of plasmid DNA expression vectors into mdx mouse skeletal muscle. Expression of dystrophin in these experiments leads to the restoration of the entire dystrophin-glycoprotein complex. This methodology was adapted for the BIO 14.6 hamster in order to test the hypothesis that introduction of normal copies of δ-SG DNA would lead to ordered sarcoglycan complex assembly. Due to the overall structural similarity of the sarcoglycan proteins to each other, each of the individual sarcoglycans was tested in this in vivo reconstitution assay.

Figure 1:
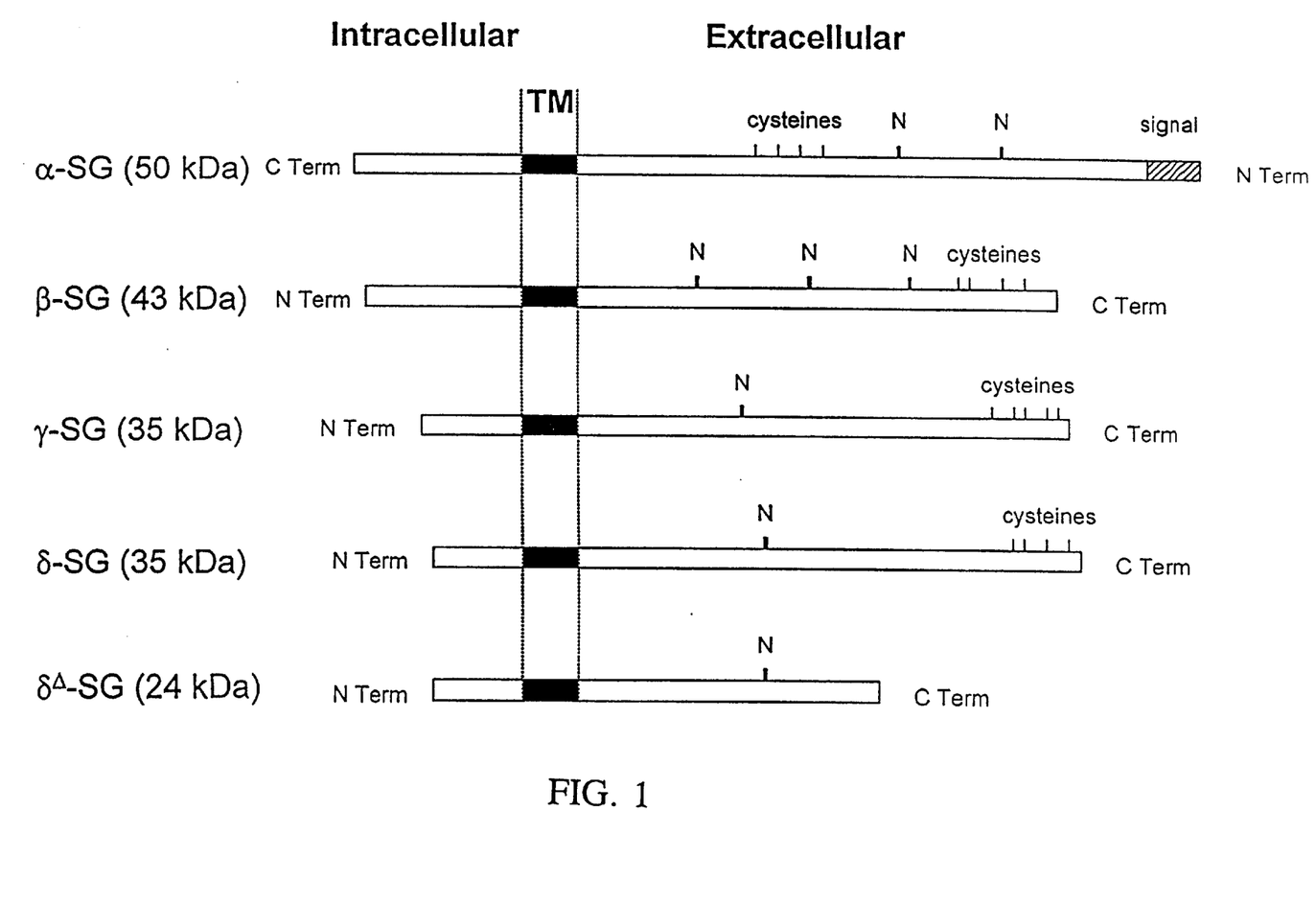
FIG. 1 is a schematic of the human sarcoglycan proteins. Putative transmembrane domains (TM), cysteine clusters (cysteines) and asparagine residues within glycosylation acceptor motifs (N) are located as indicated. α-SG is a type I transmembrane glycoprotein with a signal sequence (signal) at the amino-terminus. β-, γ-, and δ-SG are type II transmembrane glycoproteins with intracellular amino-termini and extracellular carboxyl-termini. $δ^A$-SG is truncated at the carboxyl-terminus to mimic a mutation identified for LGMD2F.

Expression vectors were engineered to encode myc epitope-tagged versions of human α-, β-, γ- and δ-SG, as well as an extracellular deletion construct ($\delta^A$-SG) which recapitulates a mutation found in LGMD2F (Nigro et al., *Nature Genet.* 14, 195–198 (1996)). A schematic representation of these proteins is shown in FIG. 1. The sarcoglycans share a similar topology, with a single putative transmembrane domain, a short intracellular domain and a larger extracellular domain. The extracellular domains contain clusters of cysteine residues, which may form intra- and intermolecular disulfide bonds, as well as consensus sequence recognition sites for asparagine-linked glycosylation. These constructs were transiently expressed in Chinese hamster ovary (CHO) cells to examine the integrity of the expressed proteins. Anti-myc immunoblot analysis of cell lysates reveals that α-, β-, γ-, δ- and $\delta^A$-SG expression vector constructs direct synthesis of proteins which fractionate by SDS-PAGE according to their predicted molecular weights. As a control, cell lysate from mock-transfected cells was shown to demonstrate specificity of the antibody for the tagged proteins.

All sarcoglycan expression constructs were co-injected with a β-galactosidase reporter construct to identify fibers that harbored the DNA constructs. Expression of δ-SG restored the sarcoglycan complex to the sarcolemma based on sarcoglycan-specific antibody detection by immunofluorescence of serial cryosections. In all δ-SG cDNA-injected animals, expression of β-galactosidase in muscle fibers was coincident with sarcoglycan expression. In contrast, fibers expressing α-, β-, γ- and $\delta^A$-SG did not have detectable sarcoglycan proteins at the sarcolemma, as determined by immunofluorscence. It is of interest to note that even overexpression of δ-SG, which is highly related at the amino acid sequence level (approximately 60% identity) to δ-SG, cannot compensate for the loss of δ-SG. Furthermore, deletion of the extracellular cysteine-rich region of δ-SG, analogous to one mutation identified for LGMD2F ($\delta^A$-SG), blocked the ability of δ-SG to rescue the sarcoglycan complex. Although this technique is limited because of the low efficiency of gene transfer (typically 1–2% of the fibers take up and express the plasmid), the data suggest that δ-SG is required for sarcoglycan complex assembly in the BIO 14.6 hamster. Finally, the results indicate that key structural determinants of δ-SG likely reside in the extracellular cysteine-rich region of the protein.

Recombinant δ-SG Adenovirus-mediated Gene Transfer into the Quadriceps Femoris Muscle of BIO 14.6 Hamster.

In order to achieve high efficiency of gene transfer, an adenovirus construct encoding human δ-SG was prepared for injection into hamster skeletal muscle. In the δ-SG adenovirus-injected BIO 14.6 muscle, the majority of the fibers were converted to δ-SG-positive. Immunofluorescence of skeletal muscle sections, using an antibody specific for δ-SG showed the extent of δ-SG localized to the sarcolemma was similar to that of unaffected control F1B hamster. In addition some cytoplasmic staining was evident, possibly due to high levels of expression generated by the CMV promoter. Renewed expression of δ-SG at the sarcolemma was coincident with the rescue of the entire sarcoglycan complex to the sarcolemma based on α-, β- and γ-SG-specific immunofluorescence of serial sections. In addition, α-DG was restored to the sarcolemma in fibers expressing δ-SG 80% or more of the fibers were converted to sarcoglycan-positive, as observed by low power field examination of immunostained muscle sections. To assess the persistence of δ-SG expression over time, hamsters were injected with the δ-SG adenovirus and examined at various time points with immunofluorescence. Remarkably, δ-SG expression was evident at all time points up to 9 months post-injection, without the use of immunosuppressive agents.

δ-SG expression resulting from hamstring injection at 11 days was compared to δ-SG expression from injection at 3-weeks. Because of the small size of the 11 day old muscle at injection and its tremendous growth over the test period, similar levels of expression as in the 3-week-old injected hamsters were not seen in the 11 day old injected hamstrings. Nevertheless, long-term expression of δ-SG following a single injection of the adenovirus was achieved with both injection ages.

These results confirm the ability of δ-SG to restore the entire sarcoglycan complex to the sarcolemma in the BIO 14.6 hamster. An adenovirus construct encoding human α-SG was also analyzed as a control. In uninjected BIO 14.6 quadriceps muscle and in BIO 14.6 quadriceps muscle injected with the α-SG adenovirus, δ-SG was not detected by immunofluorescence. Likewise, α-, β- and δ-SG proteins were not present in serial sections.

Correction of the Structural Defects in the DGC Following Rescue of the Sarcoglycan Complex in the BIO 14.6 Hamster.

Biochemical studies were performed to determine if the restored sarcoglycan complex associated correctly with other components of the DGC. Glycoprotein preparations from quadriceps muscle of F1B, BIO 14.6, and BIO 14,6 injected with $10^9$ particles of δ-SG adenovirus, were examined by immunoblot analysis using antibodies raised against δ-SG, the DGC and the 156 kDa α-dystroglycan. BIO 14.6 muscle had no detectable δ-SG and was found to have severe deficits in α-, β- and γ-SG as well as α- dystroglycan, as shown previously. After a 14 day expression period, the BIO 14.6 muscle injected with the δ-SG adenovirus exhibited renewed expression of δ-SG, the entire sarcoglycan complex, and α-dystroglycan, all at levels comparable to that of the control F1B. Equal loading of the lanes was demonstrated by comparable amounts of a non-DGC glycoprotein, the 140 kDa $α_2$ subunit of the DHPR, and silver staining.

The reconstituted DGC was further characterized by sucrose gradient sedimentation. Immunoblot analysis of the fractions, using antibody directed against either α-DG or the respective sarcoglycans, showed that α-dystroglycan from the F1B muscle sedimented as two peaks, and the sarcoglycans co-sedimented with α-dystroglycan in the later peak fractions. In contrast, α-dystroglycan from the BIO 14.6 muscle sedimented as a single peak and no sarcoglycans were present, as expected. The earlier sedimenting complex is thought to reflect a species of dystroglycan that does not associate with the sarcoglycans, possibly the dystroglycan at the myotendinous and/or neuromuscular junctions. Western blot analysis of the fractions also identified the presence of δ-, α-, β-, and γ-SG using antibodies specific for the respective proteins. This indicates that expression of δ-SG in the BIO 14.6 muscle not only restored the sarcoglycan complex to the sarcolemma, but also re-established the association between the sarcoglycan complex and α-dystroglycan as evidenced by the co-fractionation of these proteins. Together, these results provide strong evidence that the integrity of the DGC has been restored in the BIO 14.6 muscle expressing the δ-SG adenovirus.

Dystrophic Features are Greatly Reduced in Muscle Expressing δ-SG.

Figure 2:
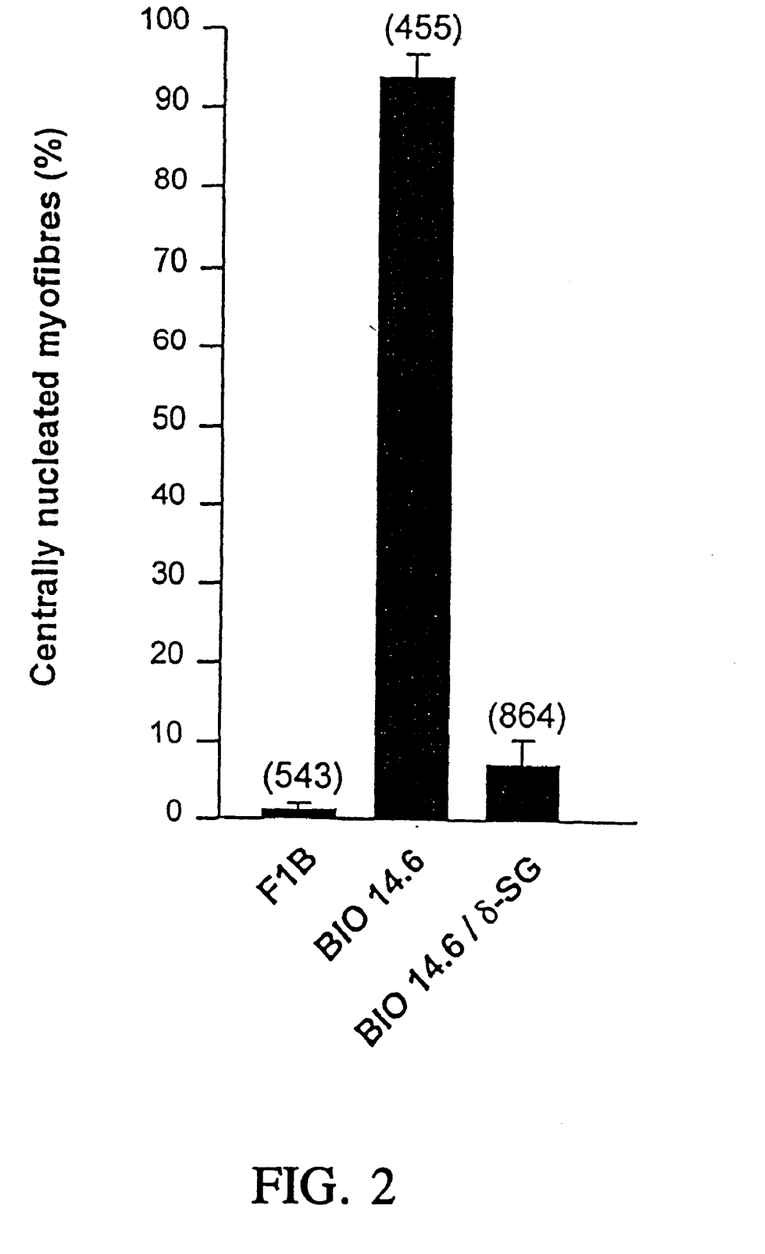
FIG. 2 is a diagrammatic representation of data from experiments measuring the percent of myofibers containing centrally located nuclei from F1B controls, BIO 14.6 hamsters, and BIO 14.6 hamsters with persistent expression of the δ-SG adenovirus. Sections from F1B, BIO 14.6 and BIO 14.6 hamsters injected with δ-SG adenovirus were examined and scored. In the case of BIO 14.6 hamsters injected with δ-SG adenovirus, only fibers converted to sarcoglycan-positive were counted. The number of fibers examined for each sample is given in parentheses and the s.e.m. is shown.

Histological features of the dystrophic muscle in the BIO 14.6 hamster include cellular infiltration, variation in myofiber size and central nucleation. Central nucleation is assumed to be a sign of continued cycles of degeneration and regeneration, with the earliest onset at 2 to 3 weeks of age in the BIO 14.6 hamster. However, genetic intervention at age three weeks resulted in a marked reduction of the number of centrally located nuclei in the injected BIO 14.6 hamster compared to uninjected BIO 14.6 littermates at 9 weeks post-injection, as determined by haematoxylon and eosin staining and immunofluorescence. The percentage of fibers with centrally-located nuclei was calculated from multiple fields of age-matched samples of F1B (1.4%), BIO 14.6 (94%) and BIO 14.6 hamsters injected with the δ-SG adenovirus (7.2%) (FIG. 2). Clearly, restoration of the sarcoglycan complex significantly affects the degenerative process in the δ-SG adenovirus-injected muscle.

Sarcolemmal Membrane Integrity is Normal in Muscle Fibers Expressing δ-SG.

An intact plasma membrane is a critical component of the highly regulated transfer of molecules into and out of muscle fibers. The stresses of contraction can induce tears in the sarcolemma, allowing for release of muscle enzymes and growth factors as well as the influx of calcium. These transient breaks are thought to be one mechanism by which skeletal muscle can sense and respond to incremental changes in external load. In the case of dystrophic muscle, chronic membrane disruptions are thought to contribute to fiber necrosis. Evidence from muscular dystrophies that arise from defects in the DGC clearly demonstrates the importance of intact molecular links between the cytoskeleton and the extracellular matrix. Perturbation of this linkage with subsequent loss of membrane integrity is an important pathogenic mechanism leading to muscle cell necrosis.

Sarcolemmal membrane permeability in live animals was assessed to evaluate its potential role in the pathogenesis of the BIO 14.6 hamster. It has been demonstrated that Evans blue dye (EBD) can be used as a tracer molecule to monitor sarcolemmal membrane integrity in various dystrophic mouse models involving the absence of dystrophin and/or utrophin. In the present study, EBD was injected intravenously into 4 month old F1B, BIO 14.6 and BIO 14.6 hamsters transfected with the δ-SG adenovirus, and dye uptake into muscle fibers was examined after 72 hours. Macroscopically, EBD incorporation into skeletal muscle was clearly visible in various muscle groups in all BIO 14.6 hamsters, whereas no dye incorporation into muscle could be detected in the F1B hamsters. The quadriceps femoris muscles of these animals were cryosectioned and analyzed by immunofluorescence. Autofluorescence of EBD was not detected in fibers from the FIB hamster. In contrast, EBD was found within groups of fibers in the BIO 14.6 hamster. Strikingly, EBD was excluded from fibers that had been converted to sarcoglycan-positive by δ-SG adenovirus (expressed for 12 weeks) in the BIO 14.6 hamster. These results demonstrate that sarcolemma membrane integrity is compromised in the BIO 14.6 hamster, but can be reversed by restoration of the sarcoglycan complex.

Generation of Sgca-null Mutant Mice.

In order to design a targeting vector to generate Sgca-null mice, the murine homologue of the human SGCA gene was isolated and cloned from a mouse skeletal muscle library. Murine and human α-sarcoglycan are highly related at the amino acid level and their expression pattern at the mRNA level is similar (Roberds et al., *Cell* 78, 625–33 (1994); Liu et al., *Biochem Biophys Res Commun* 235, 227–35 (1997)). The structural organization of the gene into ten exons is shared by both species (data not shown, Genbank #AF064081).

Targeted inactivation of one of the Sgca alleles was accomplished by replacement of exons 2 and 3 and flanking intronic sequences with the neomycin resistance gene (FIG. 1). The targeting construct was designed to create a mutant allele of Sgca representative of certain human mutations. One third of α-sarcoglycan mutations characterized to date affect exons 2 and 3 of the SGCA gene (Carrie et al., *J Med Genet* 34, 470–5 (1997); Piccolo et al., *Nature Genetics* 10, 243–245 (1995)). A total of 1023 colonies surviving G418 and gancyclovir selection were analyzed by Southern-blot analysis for the presence of homologous recombination. Using the probe shown in FIG. 1 (black box), the correctly targeted locus was shown to contain an EcoR1 fragment of 8.8 kb, while the intact allele had a 5.5 kb band. Two clones yielded chimeras producing germ-line transmission. Transmission of the mutant allele followed normal Mendelian segregation ratios for an autosomal recessive gene in mice derived from both clones. Homozygous mutant and heterozygous newborn pups appeared healthy, showing no gross developmental abnormalities compared to control littermates.

To determine if the targeting approach produced a null allele, tissues from homozygous mutants and heterozygous mice were evaluated and compared them to wild type mice. Northern blot analysis using a probe against the full length coding sequence revealed the absence of α-sarcoglycan transcript in Sgca-deficient skeletal and heart tissue from the two independently derived lines. Reverse transcription-PCR revealed the presence of a minor transcript in skeletal muscle RNA resulting from the use of cryptic splicing sites in the neomycin cassette in homozygous mutants and heterozygous mice. Sequencing of the RT-PCR product revealed that this mutant transcript encoded exon 1 and a stretch of 516 bp from the inverted neo cassette spliced with exon 4 of the Sgca gene. Unexpectedly, this aberrant splicing event inserted 172 amino acids from the non-coding strand of the neo cassette, maintaining the frame with exon 4. Translation of the altered transcript would produce a protein lacking the 91 amino acids encoded by exons 2 and 3, including part of the signal sequence. Using a C-terminal peptide antibody and mAb 20A6 against α-sarcoglycan this mutant protein could not be detected in Sgca-deficient skeletal and cardiac tissues by immunoblot or immunofluorescence analysis.

Sgca-null Mutant Mice Display a Progressive Muscular Dytrophy.

Sgca-null mutant mice did not show any overt signs of a myopathy, and were in this respect similar to mdx mice. To examine the progression of the muscular dystrophy in these mutant mice, hematoxylin and eosin stained frozen sections of the sural triceps and the diaphragm muscles between the ages of 8 days and 9 months were evaluated. Sgca-null mutant mice started to develop a progressive muscular dystrophy at one week of age and, in contrast to mdx mice, showed ongoing muscle necrosis with increasing age. Pathology characteristic of muscular dystrophy was observed in every Sgca-deficient mouse, but never in control animals. The earliest changes consisted of widely scattered clusters of necrotic myocytes or regenerating myocytes with internally placed nuclei. These clusters increased in both number and size as the mice increased in age. Based on the evaluation of 200 to 1100 myocytes per muscle, the number of non-regenerating myocytes with internally placed nuclei also increased with age. At 8 days, between 1 and 2.5% of the sural triceps and diaphragm myocytes already showed central nuclei, respectively. These numbers continuously increased and at 8 and 16 weeks of age more than 70% and as high as 99% of the Sgca-deficient myocytes contained central nuclei. In wild type mice, on the other hand, the numbers of centrally placed nuclei never exceeded 1%.

In addition to necrosis, regeneration, and central nucleation, a broad spectrum of other dystrophic changes was also noted in Sgca-deficient muscle. The most prominent of these included atrophy, hypertrophy, fiber splitting, and endomysial fibrosis. In some Sgca-deficient mice, 8 weeks of age or older, dystrophic calcification was noted in association with myocyte necrosis. Fatty infiltration was present in some of the muscles from 16 week old mice. A qualitative comparison of fiber type distribution assessed with ATPase staining as well as staining characteristics with NADH and Gomori trichrome stains suggested no substantial additional differences between null mutant and wild type mice at any age. The homozygotes from both correctly targeted cell lines demonstrated an identical dystrophic phenotype.

Sarcolemmal Integrity in α-sarcoglycan-deficient Muscle.

To test whether mutation of the α-sarcoglycan gene leads to damage of the plasma membrane, Sgca-deficient mice were intravenously injected with Evans blue dye (EBD), a normally membrane impermeant molecule. This dye penetrates into the cytoplasm of fibers with compromised sarcolemmal integrity. No obvious uptake of the blue tracer into skeletal muscles of heterozygous and control mice was detected by macroscopic inspection. In contrast, EBD uptake was consistently observed in skeletal muscle fibers of the homozygous null mutants. The extent of EBD accumulation varied among muscles. Areas of blue staining appeared mainly within the proximal limb muscles and the muscles of the pelvic and the shoulder girdle. Skeletal muscles which macroscopically showed dye uptake always revealed red EBD autofluorescence by fluorescence microscopy analysis. Most of the EBD positive fibers showed intense staining, whereas in others, the signal was faint. Interestingly, Evans blue positive fibers were distributed in clusters throughout the different muscles. Fibers that had taken up the tracer and were assumed to have pathologic plasma membrane permeability often showed characteristic features of degeneration and necrosis by H&E staining. In contrast, dye uptake was not readily visible in cardiac muscle by macroscopic inspection, and microscopic analysis revealed no EBD in cardiomyocytes of control or diseased animals.

Figure 4:
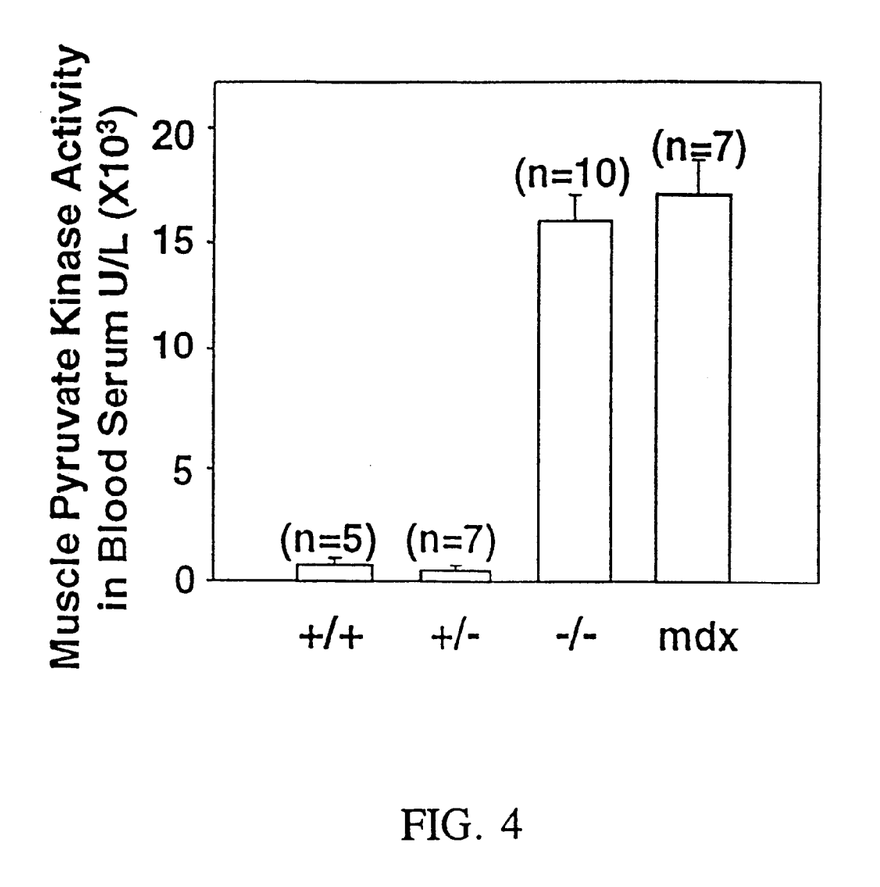
FIG. 4 is a diagrammatic representation of the activity of muscle specific pyruvate kinase (PK) in 7 to 10 week old wild type (+/+), heterozygotes (+/−), homozygotes (−/−), and mdx mice. Error bars indicate the standard deviation where n equals the number of mice in each set.

Membrane damage in 7 to 10 week old Sgca-deficient mice was also evaluated by measuring the release of muscle specific pyruvate kinase (PK) into the circulating blood (FIG. 4). Age matched wild type and heterozygous mice had normal serum levels of PK activity. Homozygous mice, on the other hand, exhibited high serum levels of PK activity similar to that of the mdx mice, indicating that membrane damage occurred to comparable extents in Sgca-null mutants as in mdx mice (FIG. 4). Similarly, in older animals (up to 18 weeks of age) no differences in PK activity between Sgca-null mice and age-matched mdx mice were found.

Loss of Sarcoglycan and Sarcospan Expression in Sgca-null Mutant Mice.

Immunofluorescence analysis was performed for each component of the sarcoglycan complex. In Sgca-deficient mice, α-sarcoglycan protein was absent from the sarcolemma of skeletal and cardiac muscle fibers. In addition, there was a concomitant drastic reduction of β-, γ- and δ-sarcoglycan. Other components of the DGC were also examined by immunofluorescence microscopy. The laminin α2 chain, α-, and β-dystroglycan were present at comparable levels with control muscle. However, the sarcolemmal staining for dystrophin was consistently patchy and reduced in Sgca-null mutant skeletal muscle compared to control, although dystrophin staining in heart appeared similar to control. Expression of the newly identified E-sarcoglycan (Ettinger et al., *J Biol Chem* 272, 32534–8 (1997)) and the 25 kD DGC component sarcospan (Crosbie, R. H. et al., *J Biol Chem* 272, 31221–4 (1997)) were also analyzed. In contrast to the other sarcoglycans, skeletal and cardiac muscle staining of E-sarcoglycan in Sgca-deficient mice was comparable to control levels. Interestingly, sarcospan was completely reduced along with the sarcoglycans at the sarcolemma of homozygous null mice, indicating a close association between the 25 kD component of the DGC and the sarcoglycan complex.

Dissociation of the DGC in Sqca-null Mutant Mice.

To further examine the expression of DGC components, immunoblot analysis was performed on isolated membrane preparations from control and homozygous mutant skeletal muscle. α-sarcoglycan muscle preparations were observed to be more susceptible to degradation by calcium dependent cysteine proteases, calpain I and II. Use of calpain I and II inhibitors allowed the preservation of protein integrity in the membrane preparations from Sgca-null mice. Coomassie blue staining and staining for caveolin-3, the dihydropyridine (DHPR), and the ryanodine receptor showed that equivalent levels of membrane proteins were present in control and homozygous mutant preparations. α-sarcoglycan was not detected in skeletal and cardiac membrane preparations from Sgca-null mice. Heterozygotes expressed control levels of α-sarcoglycan. β-, γ-, and δ-sarcoglycan were greatly reduced in α-sarcoglycan-deficient skeletal muscle membranes compared to control muscle. Dystrophin was slightly reduced in α-sarcoglycan-deficient skeletal muscle in accordance with the patchy staining observed by immunofluorescence. In accordance with the dystrophin reduction, levels of the free radical-producing enzyme neuronal nitric oxide synthase (nNOS), which is anchored to the sarcolemma by dystrophin, were also reduced. Utrophin was found at higher levels in membrane-enriched preparations from homozygous mutant mice compared to control mice. This observation could be related to the large number of regenerating fibers in Sgca-null mutant muscle, which would be expected to express higher levels of utrophin. In addition, α- and β-dystroglycan were reduced in α-sarcoglycan-deficient skeletal muscle membrane preparations compared to control mice, whereas immunofluorescence, described above, showed little dystroglycan reduction at the sarcolemma. In the supernatant from Sgca-deficient membrane preparations, α-dystroglycan was enriched and fully glycosylated, but was not tightly associated with membranes. Thus, α-dystroglycan is synthesized correctly, but is not stably anchored to the sarcolemma in the absence of the sarcoglycan complex. In addition, Western blot confirmed the immunofluorescence analysis in showing that dystrophin was no longer tightly held at the skeletal plasma membrane in the absence of the sarcoglycan complex.

Abnormal Contractile Properties of Sqca-deficient Muscles.

Figure 3:
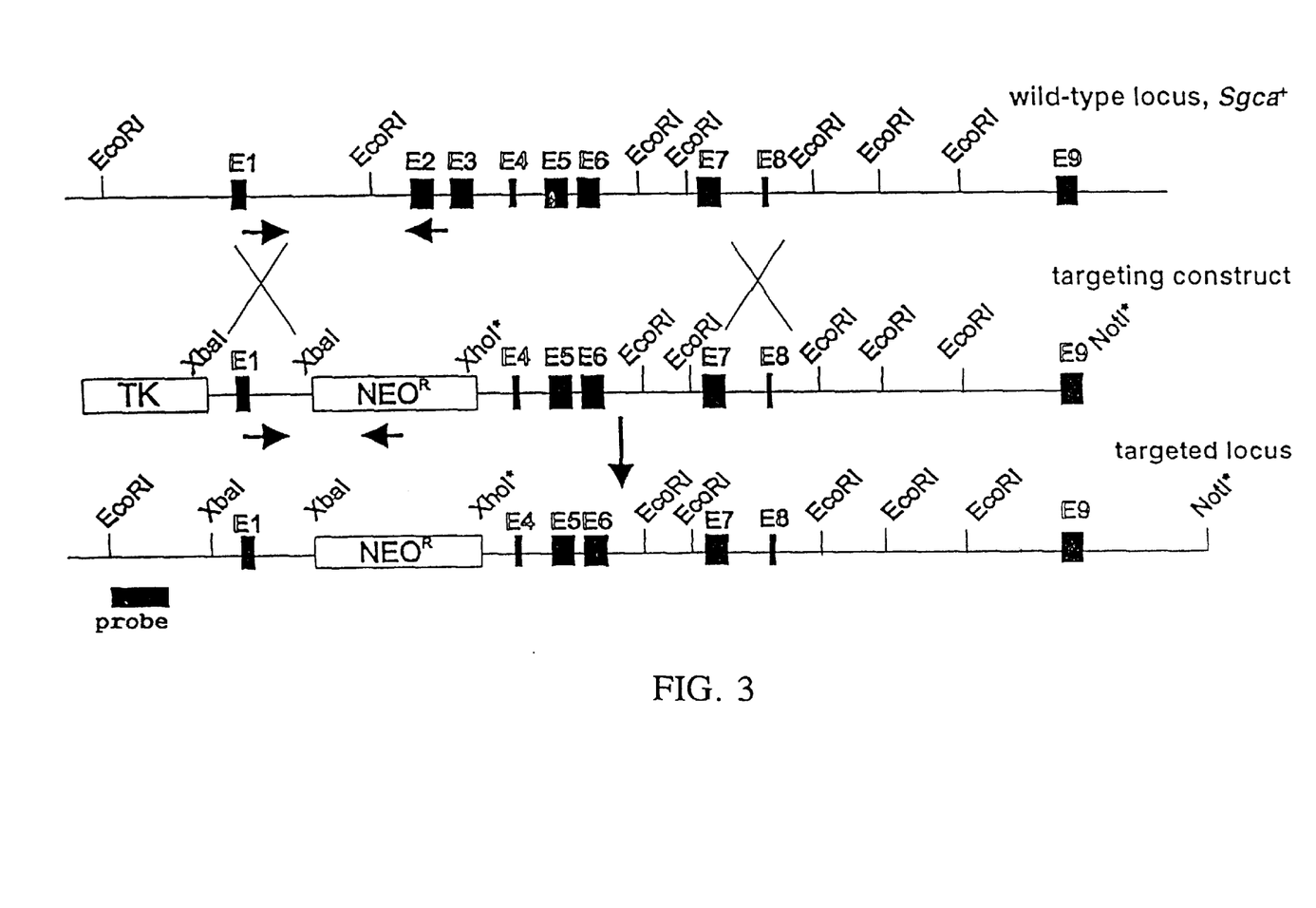
FIG. 3 is a restriction map of the wild-type Sgca locus (Sgca$^+$), the targeting construct, and the targeted locus. A region of 902 bp including exons 2 and 3 (E2, E3) was deleted and replaced by a PGK-neomycin cassette (NEO). Generation of Sgca-null mutant mice. The probe used in Southern blot analysis is depicted by the black box. Primers for PCR analysis are depicted by horizontal arrows.

The body masses of 8 weeks old Sgca-null mutant mice were 25% greater than those of their normal littermates (FIG. 3). For the long digital extensor (EDL) muscles of the Sgca-deficient mice, the masses were 55% greater than muscles of control mice. The absolute forces ($P_o$), on the other hand, revealed no differences and the specific $P_o$ in Sgca-null mice was even 25% lower than in heterozygous littermates. The resistance to stretch of the passive muscle in homozygous null mutants was 75% greater than in control animals. In contrast to the changes evident in the EDL muscles, the Sgca-null mutant soleus muscles responded in a significantly different manner. Compared with soleus muscles in normal littermates, the Sgca-null mutant soleus muscles had a 75% greater mass, a 54% greater absolute $P_o$, and no difference in either specific Po or resistance to stretch. Based on the direct measurements of muscle mass ($M_m$), muscle length ($L_m$), fiber length ($L_f$), and maximum isometric tetanic $P_o$, total fiber cross-sectional area (CSA) and specific $P_o$ were calculated. The total fiber CSA (mm$^2$) was calculated by dividing the $M_m$ (mg) by the $L_f$ (mm) and then by 1.06 (g/cm$^2$) to correct for the muscle density (Brooks et al., *J Physiol (Lond)* 404, 71–82 (1988)). The force (kN) was divided by the total fiber CSA (m$^2$) to obtain an estimate of the specific force (kN/m$^2$) of the EDL and soleus muscles.

Restoration of the Sarcoglycan Complex by Gene Transfer.

An adenovirus construct encoding human α-sarcoglycan was used to test the ability of exogenously provided α-sarcoglycan cDNA to restore the complex in α-sarcoglycan-deficient skeletal muscle. An adenovirus construct encoding human δ-sarcoglycan was used as a control. A recombinant adenovirus encoding either the human α-sarcoglycan or δ-sarcoglycan cDNA was directly injected into the quadriceps femoris of 3 week old Sgca-null mutant mice. Five days after injection, muscles were analyzed for sarcoglycan expression by immunofluorescence. In the α-sarcoglycan adenovirus-injected muscle, all components of the complex were restored at the sarcolemma in selected fibers, but the efficiency of gene replacement after several attempts was rather low compared to the results we obtained by in skeletal muscle of the BIO 14.6 cardiomyopathic hamster. To circumvent a possible immune response against the neoantigen or adenovirus itself, the α-sarcoglycan adenovirus was injected into the hamstring muscles of 2 day old Sgca-deficient pups. Immunostaining of serial transverse cryosections of injected muscle after 3 weeks revealed that high levels of renewed expression of α-sarcoglycan at the sarcolemma were observed. In addition, α-sarcoglycan positive fibers revealed expression of the entire sarcoglycan complex, sarcospan and dystrophin by immunofluorescence microscopy. The transfection efficiency was greatly improved by injecting at 2 days versus 3 weeks old (with approximately 20 to 50 times more fibers rescued). Immunostaining of the sarcoglycans was found in up to 70% of fibers, depending most likely on the delivery and the accuracy of targeting the hamstrings in the pups. However, in α-sarcoglycan-deficient quadriceps muscles injected with the δ-SG adenovirus, α-SG was not detected by immunofluorescence, nor were β-, γ-, and δ-SG. Interestingly, H&E and immunofluorescence directed at α-SG at 1 month post injection showed that central nucleation was reduced in injected Sgca-null mutant muscle. In addition, evidence of α-sarcoglycan expression over a time interval between five days and 2 months post-injection was observed.

Methods of the Invention.

Animals.

Male F1B and BIO 14.6 cardiomyopathic hamsters were obtained from BioBreeders (Fitchburg, Mass.).

Antibodies.

Rabbit 98 polyclonal antibody against α-SG has been described previously (Roberds et al.; *J. Biol. Chem.* 268: 11496 (1993)). Monoclonal antibody 20A6 recognizes α-SG (Piccolo et al.; *Nature Genet.* 5: 1963 (1995)). Monoclonal antibody 5B1 was raised against a.a. 89–152 of human β-SG (provided in collaboration with Louise Anderson). An affinity-purified rabbit antibody (Rabbit 208) was produced against a C-terminal fusion protein of rabbit γ-SG. A monoclonal antibody 21B5 was raised against a.a. 167–178 of rabbit γ-SG (provided by Louise Anderson). An affinity-purified rabbit antibody (Rabbit 215) was produced against an amino-terminal peptide of human δ-SG (MMPQEQYTHHRSTMPGAA (SEQ ID NO: 1). Rabbit 229 recognizes the carboxyl terminus of human δ-SG. Goat 20 serum (Jung et al., *J Biol Chem.* 271, 32321–32329 (1996)) and monoclonal antibody IIH6 (Roberds et al.; *J. Biol. Chem.* 268: 23739 (1993)) have been previously described.

Human Sarcoglycan Expression Constructs.

Human α-, β-, γ-, δ- and $\delta^A$-SG expression constructs were prepared by PCR (entire constructs) amplification of cDNA using primers containing appropriate restriction sites for subcloning into pcDNA3 (Pharmacia). For the $\delta^A$-SG construct, a stop codon was introduced immediately following amino acid 219. Constructs were confirmed by direct DNA sequence analysis performed by the DNA Core Facility at the University of Iowa.

Expression of SG Expression Constructs in CHO Cells.

CHO cells were transfected with the empty vector (control) or a mammalian expression vector encoding for α-, β-, γ-, δ-, and $\delta^A$-SG, engineered to include a nine amino acid myc epitope tag on the intracellular tail. Transfection was via electroporation (Holt et al., *J. Biol Chem.* 271, 8300 (1996)). Whole cell lysates were prepared and subjected to anti-myc (9E10) immunoblotting.

Recombinant Adenovirus.

The human δ-SG sequence was amplified by PCR and subcloned into the pAdCMVpA adenovirus shuttle vector. The δ-SG construct was then incorporated into an adenovirus vector and used to infect HEK293 cells by the University of Iowa Gene Transfer Vector Core. Lysates from the infected cells were collected and tested for the expression of δ-sarcoglycan protein using a δ-sarcoglycan-specific polyclonal antibody. A human α-sarcoglycan adenovirus was made and tested as a control. Recombinant viruses were plaque purified 3 times, amplified and concentrated using established methods (Davidson et al., *Exp. Neurology* 125, 258 (1994); Graham et al., *Virology* 52, 456 (1973)).

Plasmid DNA and Recombinant Adenovirus Injections.

Hamsters were anesthetized by intraperitoneal injection of sodium pentobarbital (Nembutal, Abbott Laboratories) at a calculated dose of 75 mg/kg. The skin overlying the quadriceps femoris muscle was disinfected and a 1-cm vertical incision was made. Plasmid DNA (100 μg of sarcoglycan plasmid DNA and 25 μg of β-galactosidase reporter plasmid DNA) in a total volume of 100 ul in normal saline (0.9% NaCl w/v) was injected into the quadriceps femoris muscle (Acsadi et al., *Nature* 352, 815 (1991); Danko et al., *Hum. Mol. Genet.* 2, 2055 (1993); Fritz et al., *Pediatric Research* 37, 693 (1995)). The incision was closed with 3–4 sutures. For 11 day old hamsters, the adenovirus was injected directly through the skin into the hamstring. Hamsters recovered with continual supervision and were housed post-operatively at the University of Iowa Animal Care Facility. Mice were housed in BL2 containment with isolator cages. Seven days to 9 months after injection, hamsters were euthanized by $CO_2$ asphyxiation. Injected and uninjected quadriceps femoris muscle was removed by dissection, embedded in Tissue-Tek O.C.T. compound, and quickly frozen in liquid $N_2$-cooled isopentane. For the adenovirus studies, $10^9$ viral particles in 100 μl of normal saline were injected into the quadriceps femoris muscle of 3 week-old BIO 14.6 hamsters, and details of the surgery were as outlined above. All of the above experiments were repeated in at least three animals independently.

Analysis of β-galactosidase Activity.

Serial 10 mm cryosections were fixed in 0.5% glutaraldehyde in PBS for 15 min at room temperature. After extensive washing with PBS, sections were treated with 1 mg/ml X-gal in β-galactosidase detection solution (20 mM $K_2Fe(CN)_6$, 20 mM $K_4Fe(CN)_6 \times 3H_2O$, 2 mM $MgCl_2$) for 2–4 hours. Sections were counterstained with eosin, mounted with Permount, and viewed by light microscopy.

Immunofluorescence.

Serial 7 μm cryosections were analyzed by immunofluorescence using sarcoglycan-specific antibodies as described previously (Roberds et al., *J. Biol. Chem.* 268, 23739 (1993)). For hematoxylin and eosin staining, 10 μm sections were stained for 5 min. each in hematoxylin and then eosin, dehydrated with ethanol and xylenes, mounted with Permount, and examined by light microscopy. All sections were photographed under a Zeiss Axioplan fluorescence microscope, a Leitz Diaplan fluorescence microscope, or a Bio-Rad MRC-600 laser scanning confocal microscope.

WGA-Sepharose chromatography and sucrose gradient fractionation. Quadriceps femoris muscle (1 gram) was dissected from F1B, BIO 14.6 and BIO 14.6 hamsters injected with the δ-SG adenovirus, and glycoprotein preparations were prepared (Iwata et al., *FEBS* 329, 227 (1993)). Briefly, frozen tissue was homogenized in 4 ml buffer identical or buffer A (Iwata et al., *FEBS* 329, 227 (1993)) with a polytron for 30 sec. (3×), followed by Dounce homogenization. Samples were centrifuged in a Beckman 45Ti rotor at 35,000 rpm for 37 min. The pellet was resuspended in 4 ml buffer A and the homogenization steps were repeated. The two supernatants were pooled and incubated with WGA-Sepharose at 4° C. overnight with rotation. The resin was washed and proteins were eluted with 0.4 M n-acetyl glucosamine. Eluted proteins were fractionated by centrifugation speed, length of time through a 5–30% sucrose gradient. The eluted proteins and fractions from the sucrose gradient were analyzed by immunoblotting using specific antibodies and enhanced chemiluminescence.

In vivo Membrane Permeability Assay.

Evans blue dye injections and microscopic analysis were performed as described previously (Straub et al., *J. Cell Biol.* 139, 375 (1997)), with some modifications. Evans blue dye was dissolved in phosphate-buffered saline (10 mg/ml) and sterilized by passage through membrane filters with a pore size of 0.2 μm. Hamsters were anesthetized by intraperitoneal injection of sodium pentobarbital (Nembutal, Abbott Laboratories) at a calculated dose of 75 mg/kg. Subsequently 0.25 μl/10 g body weight of the dye solution was injected intravenously through the front limb vein. Animals were euthanized 72 hours after injection by asphyxiation with gaseous $CO_2$. All dye-injected hamsters were skinned and inspected for dye uptake in the skeletal muscles, by the appearance of blue staining. Muscle sections for microscopic Evans blue detection were incubated in ice cold acetone at −20° C. for 10 min., washed in PBS and mounted with Vectashield (Vector Laboratories). All sections were examined and photographed under a Zeiss Axioplan fluorescence microscope.

NULL MUTANT EXPERIMENTS

Isolation of α-sarcoglvcan and Vector Construction.

The α-sarcoglycan gene was isolated from a λ FIXII 129/sv genomic skeletal muscle library by homology screening using a radiolabeled human α-sarcoglycan cDNA. A 16.2 kb NotI fragment was characterized by restriction mapping and limited sequencing (Genbank# AF064081). Two StyI fragments of 0.16 and 0.9 kb carrying exon 1 and a portion of 5' and 3' contiguous intron were co-ligated into the XbaI site of pPNT. Orientation of the two inserted fragments was checked by PCR and sequencing. A 9 kb fragment containing a portion of intron 3, and exon 4 to exon 9 was amplified using a high fidelity PCR reaction (Takara) with intron 3 forward primer from: CCCCTCGAGCCGTTCCTCAGACTTTTTATTC(SEQ ID NO: 2) and exon 9 reverse primer from: AATGCGGCCGCTCTCCTGTACGAACAT(SEQ ID NO: 3). The PCR fragment was restriction digested by NotI and XhoI and inserted into a XhoI-NotI cut plasmid. Correct targeting replaced exon 2 (containing part of the signal sequence), exon 3, 571 bp of intron 1 and 65 bp of intron 3 with a neomycin resistance gene in opposite transcriptional orientation (FIG. 3).

Generation of Sqca-deficient Mice.

The NotI linearized construct was introduced into $2 \times 10^7$ $R_1$ ES cells by electroporation (240V, 500μF; Bio-Rad Gene Pulser). The ES 30 cells were maintained on feeder layers and passaged clonally. Targeting fidelity was determined by Southern analysis, which was performed using the probe shown (black box) in FIG. 3. Cells from three correctly targeted clones were microinjected into C57BL/6J blastocysts and transferred into pseudopregnant recipients. Following germ-line transmission, genotypes were determined by PCR on DNA from tail biopsies. Primer sites are shown in FIG. 3 as horizontal arrows. The following primers and PCR conditions were used: C-KO2 in intron 1: CAGGGCTGGGAGCTGGGTTCTG(SEQ ID NO: 4); MFD1 in intron3 (deleted in the null allele): CCCAGGGCCTTGATGCCT(SEQ ID NO: 5); and NEOTR: GCTATCAGGACATAGCGTTGGC TA(SEQ ID NO: 6): first denaturation at 94° C. for 5 min; followed by 30 cycles of 1 min, 94° C., 1 min 64° C., 2 min 30 sec at 72° C., and 7 min last extension at 72° C. Wild type and null alleles corresponded to PCR fragments of 1061 bp and 618 bp respectively.

Northern-blot Analysis.

Total RNA from control, heterozygous, and homozygous null mutant skeletal and cardiac tissues was extracted using RNAzol (Tel-Test) according to manufacturer specifications. 30 μg of total RNA was run on a 1.25% agarose gel containing 5% formaldehyde and transferred to Hybond N membrane (Amersham). RNA was cross-linked to the membrane using a Stratagene UV crosslinker. Membranes were then prehybridized and hybridized using standard methods. Washes were carried out at 65° C. in 1×SSC/1% SDS initially, then 0.1×SSC/0.1% SDS. Blots were exposed for autoradiography.

Evans Blue Dye Injection and Microscopic Evaluation.

Evans blue (Sigma Chemical Co., St. Louis, Mo.) was dissolved in PBS (10 mg/ml) and sterilized by passage through membrane filters with a pore size of 0.2 μm. Mice were injected intravenously with 0.25 μl/10 g body weight of the dye solution through the tail vein. Animals were sacrificed 6 hours after injection by cervical dislocation. During the time period between injection and cervical dislocation, animals were kept in standard laboratory cages. All mice were skinned and inspected for dye uptake in the skeletal muscles, indicated by blue coloration. Muscle sections for microscopic Evans blue detection were incubated in ice cold acetone at −20° C. for 10 min, and after a rinse with PBS, sections were mounted with Vectashield mounting medium (Vector). Sections were observed under a Zeiss Axioplan fluorescence microscope (Carl Zeiss, Inc., Thornwood, N.Y.) or a MRC-600 laser scanning confocal microscope (Bio Rad Laboratories, Hercules, Calif.).

Pyruvate Kinase Assay.

Activities of muscle specific pyruvate kinase isozyme found in the blood serum were measured as previously documented (Edwards et al., Clin Chem. 27, 906–909 (1981)). Blood was collected from the retroorbital sinus of 2 to 18 week old mice and the serum was stored at −80° C. prior to measurements.

Antibodies.

Monoclonal antibodies IIH6 against α-dystroglycan (Ervasti et al., Cell 66, 1121–1131 (1991)) and 8D5 against β-dystroglycan (Lim et al., Nature Genetics 11, 257–265 (1995)) were previously characterized. Monoclonal antibodies 20A6 against α-sarcoglycan, 5B1 against β-sarcoglycan, and 21B5 against γ-sarcoglycan were generated in collaboration with Louise Anderson. The monoclonal antibody against caveolin-3 was purchased from Transduction Laboratories. Rabbit polyclonal antibodies against α-sarcoglycan (Roberds et al., J Biol Chem 268, 23739–23742 (1993)), dystrophin and utrophin (Ohlendieck et al., Neuron 7, 499–508 (1991)), nNOS (Crosbie et al., Hum Mol Genet 7, 823–9 (1998)), $α_1$-DHPR (Ohlendieck et al., J Cell Biol 112, 135–148 (1991)), and the laminin α2 chain (Allamand et al., Hum Mol Genet 6, 747–52 (1997)) were described previously. Two affinity-purified rabbit antibodies (Rabbit 208 and 215) were produced against a C-terminal fusion protein of γ-sarcoglycan, and against an N-terminal peptide (MMPQEQYTHHRSTMPGAA(SEQ ID NO: 1)) of δ-sarcoglycan affinity-purified rabbit antibody respectively. An affinity-purified goat antibody (Goat 26) was produced against a N-terminal fusion protein of β-sarcoglycan containing amino acids 1 to 65. Polyclonal antibodies against α-dystroglycan fusion protein D (Ibraghimov-Beskrovnaya et al., Nature 355, 696–702 (1992)) were affinity-purified from goat 20. An affinity-purified rabbit antibody (Rabbit 235) was produced against a C-terminal fusion protein of sarcospan (CFVMWKHRYQVFYVGVGLRSLMASDGQLPKA SEQ ID NO: 7). Two polyclonal antibodies against ε-sarcoglycan were used. One was previously characterized (Ettinger et al., J Biol Chem 272, 32534–8 (1997)) and one was obtained from affinity purified rabbit antibody (Rabbit #232) against a C-terminal peptide of E-sarcoglycan (PHQTQIPQQQTTGKWYP SEQ ID NO: 8).

Immunofluorescence Analysis.

For immunofluorescence, 7 μm transverse cryosections were prepared from control and Sgca-null mutant skeletal and cardiac muscle. All procedures were performed at room temperature. Sections were blocked with 5% BSA in PBS for 1 hr., and then incubated with the primary antibodies for 90 min. After washing with 1% BSA/PBS, sections were incubated with Cy3-conjugated secondary antibodies (1:250) for 1 hr., washed with 1% BSA/PBS. After a rinse with PBS, sections were mounted with Vectashield mounting medium (Vector) and observed under a Zeiss Axioplan fluorescence microscope.

Contractile Properties.

Figure 5:
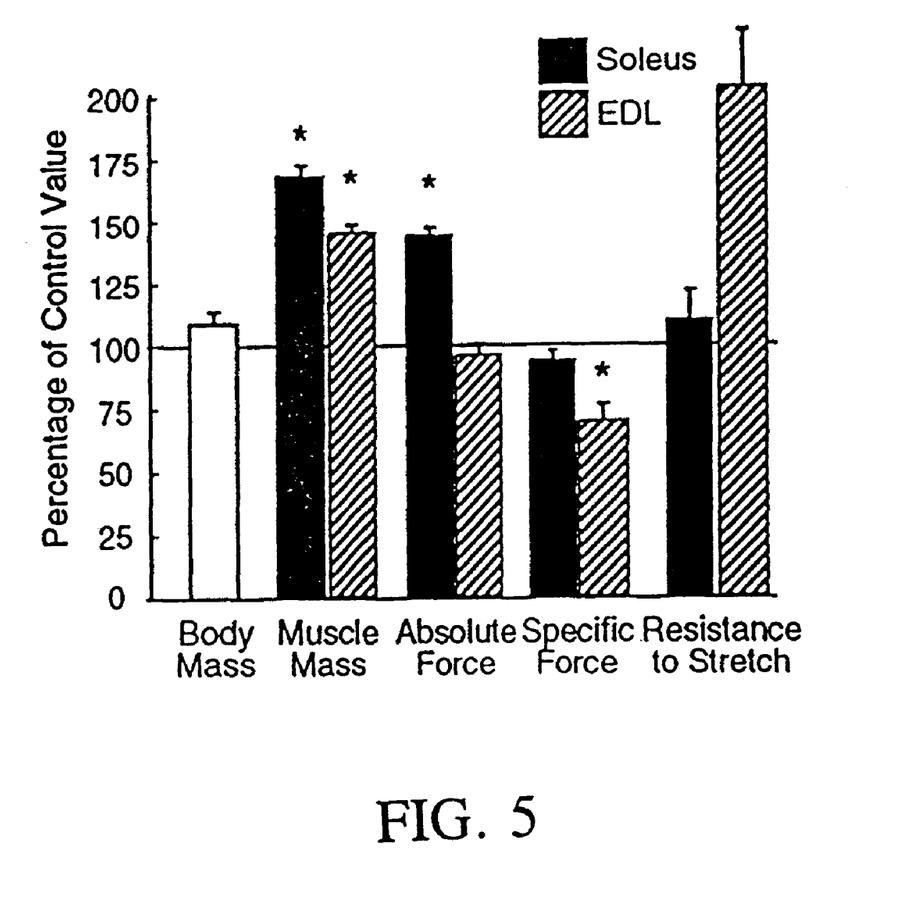
FIG. 5 is a diagrammatic representation of data on body mass, muscle mass, absolute maximum isometric tetanic force, specific force, and peak force during resistance to stretch of passive muscles for the different mice assayed. The data on EDL and soleus muscles of the Sgca-null mutant mice are represented as a percentage of the values for muscles of control mice. Significant differences between the data obtained in Sgca-deficient and control mice are indicated by an asterisk. All data are presented as the mean ± one standard error of the mean.

For the measurement of contractile properties of EDL or soleus muscles of control or Sgca-deficient mice in vitro, mice were anesthetized with sodium pentobarbital (30 to 50 mg/kg for control or Sgca-deficient mice, respectively). Supplemental doses of the anesthetic were given as required to maintain a level of anesthesia sufficient that mice did not respond to tactile stimuli. Prior to the measurement of the contractile properties, each mouse was weighed. Contractile properties were measured on 28 muscles, 6 EDL and 6 soleus muscles from control and 8 EDL and 8 soleus muscles from Sgca-null mutant mice. The muscles were isolated and removed carefully from the anesthetized mice and immersed in an oxygenated (95% $O_2$ and 5% $CO_2$) bath containing a buffered mammalian Ringer's solution (pH 7.4), which included curare. The solution was maintained at 25° C. The tendons were tied securely to a servomotor and a force transducer. The muscles were stimulated directly by the current flow between two large platinum electrodes (Brooks et al., *J Physiol (Lond)* 404, 71–82 (1988)). The voltage of the stimulator was set to provide maximum twitch force and the $L_m$ was set at optimum length ($L_o$) for force development. With the muscle at $L_o$, the frequency of stimulation was increased until force plateaued at $P_o$. Following the measurement of $P_o$, the length of the muscle was set at 90% of $L_f$ and with the muscle passive the muscle was stretched to 110% of $L_f$ at 1 $L_f$/s and then returned at the same velocity to 90% of $L_f$. The peak force at the end of the stretch was used as a measure of the resistance to stretch of the passive muscle. The muscle was removed from the bath, blotted and weighed to obtain the $M_m$. Each percentiled data set was analyzed by a two way analysis of variance (ANOVA) in a general linear model algorithm appropriate for unequal sample sizes (Statistical Analysis System, Gary, N.C.). In circumstances where the overall F-ratio for the ANOVA was significant, the differences between individual group means were determined by post hoc pairwise t-comparisons of least square means with appropriate correction of the significance level to account for multiple comparisons. Significant differences between data on control and Sgca-deficient mice are indicated in FIG. 5 by asterisks and the differences between the EDL and the soleus muscles are indicated with a sword. Significance was set a priori at $p<0.05$.

Recombinant Adenovirus Injections.

The human α-sarcoglycan CDNA sequence was subcloned into the pAdRSVpA adenovirus vector through standard methods of homologous recombination with Ad5 backbone dl309 by the University of Iowa Gene Transfer Vector Core. Lysates from the infected cells were collected and tested for the expression of α-sarcoglycan using a polyclonal antibody. Recombinant viruses were plaque purified 3 times, amplified and concentrated using established methods (Davidson et al., *Exp Neurol* 125, 258–67 (1994); Graham et al., *Virology* 54, 536–9 (1973)). Recombinant adenovirus injections were performed as previously described (Holt et al., *Mol Cell* 1, 841–848 (1998)). For 2 day old Sgca-null mutant mice, the adenovirus was injected directly through the skin into the hamstring. Three week old mice were anesthetized by intraperitoneal injection of sodium pentobarbital (Nembutal, Abbott Laboratories) at a calculated dose of 50 mg/kg. A human δ-sarcoglycan adenovirus was used as control.

Serial transverse cryosections of injected muscle after 3 weeks, were stained with the following antibodies: α-sarcoglycan (α-SG), β-sarcoglycan (β-SG), γ-sarcoglycan (γ-SG), and δ-sarcoglycan (δ-SG), dystrophin (DYS) and sarcospan (SPN).

Reduction of central nucleation in fibers expressing recombinant α-sarcoglycan adenovirus was detected in two day old homozygous mutant mice that were injected as described above. Quadriceps muscles were analyzed 1 month post-injection by H&E and immunofluorescence using a polyclonal antibody against α-sarcoglycan (α-SG), 1 month post-injection.

Immunoblot Analysis of Membrane Enriched Preparations.

Crude surface membranes from skeletal and cardiac muscle were prepared as described previously (Ohlendieck et al., *Journal of Cell Biology* 112, 135–148 (1991)). Membranes were resolved by SDS-polyacrylamide gel electrophoresis (SDS-PAGE) on 3–12% linear gradient gel and transferred to nitrocellulose membrane. Immunoblot staining was performed as previously described (Ohlendieck et al., *Journal of Cell Biology* 112, 135–148 (1991)).

GenBank Accession Numbers.

The GenBank accession number for the mouse genomic sequence of α-SG gene is: AF064081.

What is claimed is:

1. A method for treating an individual for sarcoglycan-deficient limb-girdle muscular dystrophy caused by an autosomal recessive mutation in the alpha-sarcoglycan gene of the individual, comprising the steps:
   a) providing an expression vector which contains nucleic acid sequences encoding a functional alpha-sarcoglycan protein; and
   b) introducing the expression vector into skeletal muscle tissue of the individual by intramuscular injection, under conditions appropriate for expression of the alpha-sarcoglycan protein, wherein said expression results in restoration of the sarcoglycan complex within the skeletal muscle tissue.

2. The method of claim 1 wherein the expression vector is selected from the group consisting of an adenovirus expression vector, a gutted adenovirus expression vector and an adeno-associated expression vector.

3. The method of claim 1 where the expression vector contains a muscle tissue-specific promoter.

4. A method for treating an individual for sarcoglycan-deficient limb-girdle muscular dystrophy caused by an autosomal recessive mutation in the delta-sarcoglycan gene of the individual, comprising the steps:
   a) providing an expression vector which contains nucleic acid sequences encoding a functional delta-sarcoglycan protein; and
   b) introducing the expression vector into skeletal muscle tissue of the individual by intramuscular injection, under conditions appropriate for expression of the delta-sarcoglycan protein, wherein said expression results in restoration of the sarcoglycan complex within the skeletal muscle tissue.

5. The method of claim 4 wherein the expression vector is selected from the group consisting of an adenovirus expression vector, a gutted adenovirus expression vector and an adeno-associated expression vector.

6. The method of claim 4 where the expression vector contains a muscle tissue-specific promoter.

* * * * *